United States Patent
Takezaki et al.

(10) Patent No.: US 10,751,027 B2
(45) Date of Patent: Aug. 25, 2020

(54) ULTRASOUND PROBE, PERFORMANCE EVALUATION METHOD THEREFOR, AND ULTRASOUND DIAGNOSTIC EQUIPMENT

(71) Applicant: Hitachi, Ltd., Tokyo (JP)

(72) Inventors: Taiichi Takezaki, Tokyo (JP);
Shuntaro Machida, Tokyo (JP);
Daisuke Ryuzaki, Tokyo (JP)

(73) Assignee: HITACHI, LTD., Tokyo (JP)

( * ) Notice: Subject to any disclaimer, the term of this patent is extended or adjusted under 35 U.S.C. 154(b) by 700 days.

(21) Appl. No.: 15/325,489

(22) PCT Filed: Jun. 19, 2015

(86) PCT No.: PCT/JP2015/067746
§ 371 (c)(1),
(2) Date: Jan. 11, 2017

(87) PCT Pub. No.: WO2016/009783
PCT Pub. Date: Jan. 21, 2016

(65) Prior Publication Data
US 2017/0156696 A1    Jun. 8, 2017

(30) Foreign Application Priority Data

Jul. 16, 2014    (JP) ................. 2014-146192

(51) Int. Cl.
*A61B 8/00* (2006.01)
*G01B 17/02* (2006.01)
(Continued)

(52) U.S. Cl.
CPC .......... *A61B 8/4483* (2013.01); *A61B 8/4444* (2013.01); *A61B 8/5207* (2013.01);
(Continued)

(58) Field of Classification Search
CPC ... A61B 8/4444; A61B 8/4483; A61B 8/4494; A61B 8/5207; A61B 8/58; B06B 1/0292; G01B 17/02; G01B 21/045; G01B 7/14
See application file for complete search history.

(56) References Cited

U.S. PATENT DOCUMENTS

| | | | |
|---|---|---|---|
| 6,564,643 B1 | 5/2003 | Horie et al. | |
| 6,958,255 B2 | 10/2005 | Khuri-Yakub et al. | |

(Continued)

FOREIGN PATENT DOCUMENTS

| | | |
|---|---|---|
| JP | 3567089 B2 | 9/2004 |
| JP | 2006-516368 A | 6/2006 |

(Continued)

OTHER PUBLICATIONS

International Preliminary Report on Patentability received in corresponding International Application No. PCT/JP2015/067746 dated Jan. 26, 2017.

(Continued)

*Primary Examiner* — Amanda K Hulbert
(74) *Attorney, Agent, or Firm* — Mattingly & Malur, PC

(57) ABSTRACT

Technique that enables precisely measuring cavity height and precisely grasping maximum transmission sound pressure in an ultrasonic probe is provided to the ultrasonic probe using CMUT. The ultrasonic probe according to the present invention includes plural cells each of which includes a lower electrode and an upper electrode arranged via a gap with respect to the lower electrode, and the plural cells include an ultrasonic cell the gap of which is void and which transmits/receives an ultrasonic wave and a reference cell the gap of which is filled with a conductive material. Electrostatic capacity of the ultrasonic cell and the reference cell is measured, parasitic capacity included in the measured electrostatic capacity as to the ultrasonic cell is corrected using parasitic capacity included in the measured electro- (Continued)

static capacity as to the reference cell, and cavity height is calculated on the basis of the corrected electrostatic capacity of the ultrasonic cell.

7 Claims, 12 Drawing Sheets

(51) Int. Cl.
*B06B 1/02* (2006.01)
*G01B 21/04* (2006.01)
*A61B 8/08* (2006.01)
*G01B 7/14* (2006.01)

(52) U.S. Cl.
CPC .............. *A61B 8/58* (2013.01); *B06B 1/0292* (2013.01); *G01B 7/14* (2013.01); *G01B 17/02* (2013.01); *G01B 21/045* (2013.01); *A61B 8/4494* (2013.01)

(56) References Cited

U.S. PATENT DOCUMENTS

| 2004/0085858 A1 | 5/2004 | Khuri-Yakub et al. |
| 2010/0137719 A1* | 6/2010 | Ikeda .................. A61B 8/4483 600/459 |

FOREIGN PATENT DOCUMENTS

| JP | 2008-080442 A | 4/2008 |
| JP | 2010-098454 A | 4/2010 |
| JP | 2012-511963 A | 5/2012 |
| JP | 2014-072554 A | 4/2014 |
| WO | 2008/136198 A1 | 11/2008 |
| WO | 2010/082993 A2 | 7/2010 |

OTHER PUBLICATIONS

International Search Report of PCT/JP2015/067746 dated Sep. 29, 2015.

* cited by examiner (a)

(b)

ULTRASOUND PROBE, PERFORMANCE EVALUATION METHOD THEREFOR, AND ULTRASOUND DIAGNOSTIC EQUIPMENT

TECHNICAL FIELD

The present invention relates to an ultrasonic probe provided to an ultrasonic diagnostic apparatus, and especially relates to technique for enhancing precision of an ultrasonic probe in which plural transducer units are arrayed like a two-dimensional array.

BACKGROUND ART

A piezoelectric ceramic represented by zinc zirconate titanate (PZT) has been used for a probe of an ultrasonic diagnostic apparatus as an electroacoustic transducer that transmits/receives an ultrasonic wave. Recently, however, a capacitive micromachined ultrasonic transducer (CMUT) having broader-band characteristics than piezoelectric ceramic is widely noticed, and its research and development are promoted (for example, refer to Patent Literature 1).

The CMUT has structure in which an upper electrode is formed on the upside of a lower electrode formed on a substrate with a cavity between the electrodes and the cavity is covered with an insulating film, and is a piezoelectric transducer making use of electrostatic force generated on a membrane on the upside of the cavity by applying voltage between the upper electrode and the lower electrode and causing potential difference. The transmission of an ultrasonic wave is performed because electrostatic force applied to the membrane varies by temporally varying voltage applied to the upper and lower electrodes and the variation oscillates the membrane, and the reception of an ultrasonic wave is performed by detecting displacement of the membrane as voltage variation or current variation in a state in which fixed voltage is applied between the upper and lower electrodes.

In an ultrasonic diagnostic apparatus, maximum transmission sound pressure is important performance that determines imageable maximum depth. Maximum transmission sound pressure of the CMUT is determined by maximum displacement of the membrane, that is, cavity height. Therefore, to acquire desired maximum transmission sound pressure, it is important to secure the cavity height and it is required to measure the precise cavity height. Further, in an ultrasonic probe, multiple transducer units are normally arrayed in a two-dimensional array, and it is required that these transducer units can generate the same ultrasonic waves at the same applied voltage.

CITATION LIST

Patent Literature

Patent Literature 1: Japanese Unexamined Patent Application Publication (Translation of PCT Application) No. 2006-516368

SUMMARY OF INVENTION

Technical Problem

To acquire desired maximum transmission sound pressure, it is demanded to measure precise height of a cavity. Although no method of measuring precise height of a cavity is established, a method of estimating height of a cavity on the basis of a shape of a membrane and a method of calculating on the basis of electrostatic capacity and the like are conceivable, for example. However, in the former method, since the cavity height is not directly measured, the precision is insufficient. Further, in the latter method, when parasitic capacity except cells of CMUT is included in the measured electrostatic capacity, the precise cavity height cannot be measured.

The present invention has it as its object to provide technique for enabling measuring precise height of a cavity in CMUT and hereby, precisely grasping maximum transmission sound pressure in an ultrasonic probe.

Solution to Problem

To settle the abovementioned problems, the invention is provided with a reference cell that enables estimating parasitic capacity separately from an ultrasonic cell that transmits/receives an ultrasonic wave in the ultrasonic probe. Precision of the measurement of cavity height is enhanced by correcting cavity height calculated on the basis of electrostatic capacity of the ultrasonic cell using measured electrostatic capacity as to the reference cell.

That is, the ultrasonic probe according to the present invention includes a transducer where plural cells each of which has a lower electrode and an upper electrode arranged via a gap with respect to the lower electrode are arrayed, and has a characteristic that the plural cells include the ultrasonic cell the gap of which is void and which transmits/receives an ultrasonic wave and the reference cell in which the gap is filled with a conductive material.

Further, a performance evaluation method according to the present invention is based upon a method of evaluating the cavity height of the ultrasonic cell in the ultrasonic probe which includes the transducer where plural cells each of which has the lower electrode and the upper electrode arranged via a gap with respect to the lower electrode are arrayed and in which the plural cells include the ultrasonic cell the gap of which is void and which transmits/receives an ultrasonic wave and the reference cell the gap of which is filled with a conductive material in the plural cells, and has a characteristic that the performance evaluation method includes a step of measuring electrostatic capacity of the ultrasonic cell and the reference cell, a step of correcting parasitic capacity included in the measured electrostatic capacity as to the ultrasonic cell using parasitic capacity included in the measured electrostatic capacity as to the reference cell, and a step of calculating the cavity height on the basis of the corrected electrostatic capacity of the ultrasonic cell.

The ultrasonic diagnostic apparatus according to the present invention includes the abovementioned ultrasonic probe and preferably includes a performance evaluation device that evaluates the cavity height in the ultrasonic cell utilizing the reference cell.

Advantageous Effects of Invention

According to the present invention, maximum transmission sound pressure in the ultrasonic probe can be precisely grasped.

BRIEF DESCRIPTION OF DRAWINGS

FIG. 14(a) is a plan view, and FIG. 14(b) is a sectional view viewed along a line A-A' in FIG. 14(a).

DESCRIPTION OF EMBODIMENTS

An ultrasonic probe in this embodiment uses CMUT for an ultrasonic transducer. Plural cells configuring the CMUT are respectively provided with a lower electrode and an upper electrode arranged via a gap with respect to the lower electrode, and have a characteristic that an ultrasonic cell the gap of which is void and which transmits/receives an ultrasonic wave and a reference cell the gap of which is filled with a conductive material are included. Further, the ultrasonic diagnostic apparatus in this embodiment has a characteristic that the ultrasonic probe having this characteristic is used.

The ultrasonic probe in this embodiment can reduce an effect of parasitic capacity by correcting measured electrostatic capacity as to the ultrasonic cell using measured electrostatic capacity as to the reference cell and can acquire the precise height of the ultrasonic cell on the basis of the corrected electrostatic capacity. The ultrasonic diagnostic apparatus in this embodiment can set suitable driving voltage by using the abovementioned ultrasonic probe and in addition, can suitably manage the ultrasonic probe.

Figure 1:
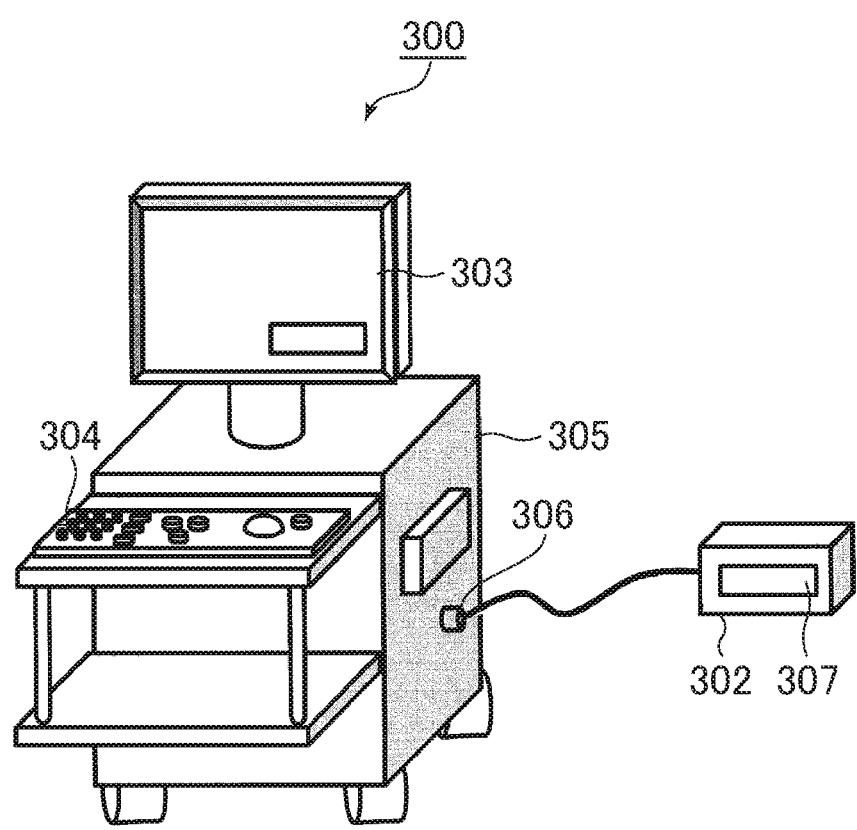
FIG. 1 is a perspective view showing the whole configuration of an ultrasonic diagnostic apparatus to which the present invention is applied.

First, referring to FIGS. 1 and 2, a configuration of the ultrasonic diagnostic apparatus in this embodiment will be described. FIG. 1 is a perspective view showing the whole configuration of the ultrasonic diagnostic apparatus and FIG. 2 is a block diagram showing functions of the ultrasonic diagnostic apparatus.

As shown in FIG. 1, the ultrasonic diagnostic apparatus 300 includes a main body 305 which houses an ultrasonic transmitter-receiver circuit that transmits/receives an ultrasonic wave, a signal processing circuit that processes an echo signal received by the ultrasonic transmitter-receiver circuit and generates an ultrasonic image as an object of medical examination and the like, a display 303 which is connected to the main body 305 and which displays GUI for an interface between the ultrasonic image and an operator, an operator console 304 for the operator to operate, and the ultrasonic probe 302 connected to the ultrasonic transmitter-receiver circuit via a connector 306 fixed to the main body 305. The ultrasonic probe 302 transmits/receives an ultrasonic wave to/from an examinee in a state in which the ultrasonic probe is touched to the examinee and includes an ultrasonic transducer 307 having structure in which multiple transducer units are arranged like a two-dimensional array, an acoustic lens, and a packing material. In the ultrasonic diagnostic apparatus in this embodiment, the CMUT is used for the ultrasonic transducer 307.

In FIG. 1, the mobile ultrasonic diagnostic apparatus provided with wheels at the bottom of the main body 305 is shown for example. However, this embodiment can be applied to an ultrasonic diagnostic apparatus fixed to a clinical laboratory, a laptop or box-type mobile ultrasonic diagnostic apparatus, and a well-known ultrasonic diagnostic apparatus.

Figure 2:
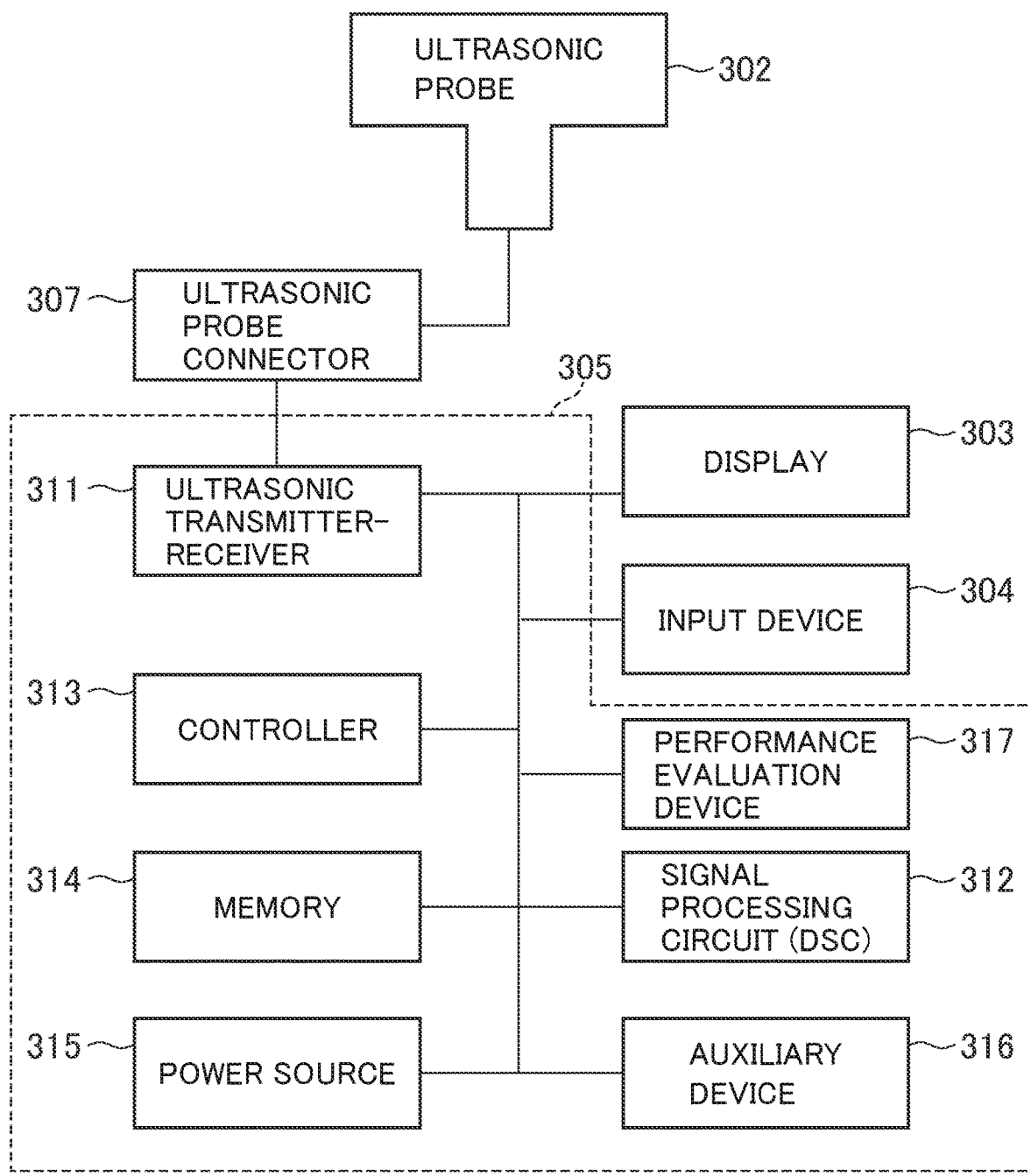
FIG. 2 is a functional block diagram showing the ultrasonic diagnostic apparatus according to the present invention.

As shown in FIG. 2, the ultrasonic transmitter-receiver circuit (the ultrasonic transmitter-receiver) 311, the signal processing circuit (the signal processor) 312, a controller 313, a memory 314, a power source 315, and an auxiliary device 316 are provided to the main body 305.

The ultrasonic transmitter-receiver circuit 311 generates driving voltage for transmitting an ultrasonic wave from the ultrasonic probe 302, receives a signal from the ultrasonic probe 302, and includes a delay circuit, a filter, a gain control circuit and the like. The signal processing circuit 312 applies processing required for compressing a log, correction such as correcting depth, imaging and the like to a received echo signal and may also include a digital scan converter (DSC), a color Doppler circuit, an FFT analyzer and the like. The signal processing circuit 312 can process both an analog signal and a digital signal, a part of the circuit can be realized by software or can also be realized by an application specific integrated circuit (ASIC) and a field-programmable gate array (FPGA).

The controller 313 controls each circuit of the main body 305 and the devices connected to the main body 305. In the memory 314, information and parameters required for signal processing and control and results of processing are stored. The power source 315 supplies electric power required for each unit of the ultrasonic diagnostic apparatus. The auxiliary device 316 is provided so as to realize a function associated with the ultrasonic diagnostic apparatus, for example, generation of voice and is suitably added if necessary.

In addition to the abovementioned functions, a performance evaluation function (a performance evaluation device 317) of the ultrasonic probe 302 can be provided to the ultrasonic diagnostic apparatus 300 in this embodiment. The performance evaluation function of the ultrasonic probe 302 will be described later.

The ultrasonic diagnostic apparatus in this embodiment has a characteristic that the CMUT provided with the reference cell in addition to the ultrasonic cell that transmits/receives an ultrasonic wave is adopted for an ultrasonic transducer of the ultrasonic probe. As for an array of cells and a feeding method, various modes can be adopted. Each embodiment of the ultrasonic probe will be described below.

First Embodiment

In an ultrasonic probe equivalent to a first embodiment, a reference cell is arranged at the end of ultrasonic cells arrayed like a two-dimensional array, and the ultrasonic cells and the reference cell share a lower electrode. Referring to the drawings, structure of the ultrasonic probe in this embodiment will be described in detail.

Figure 3:
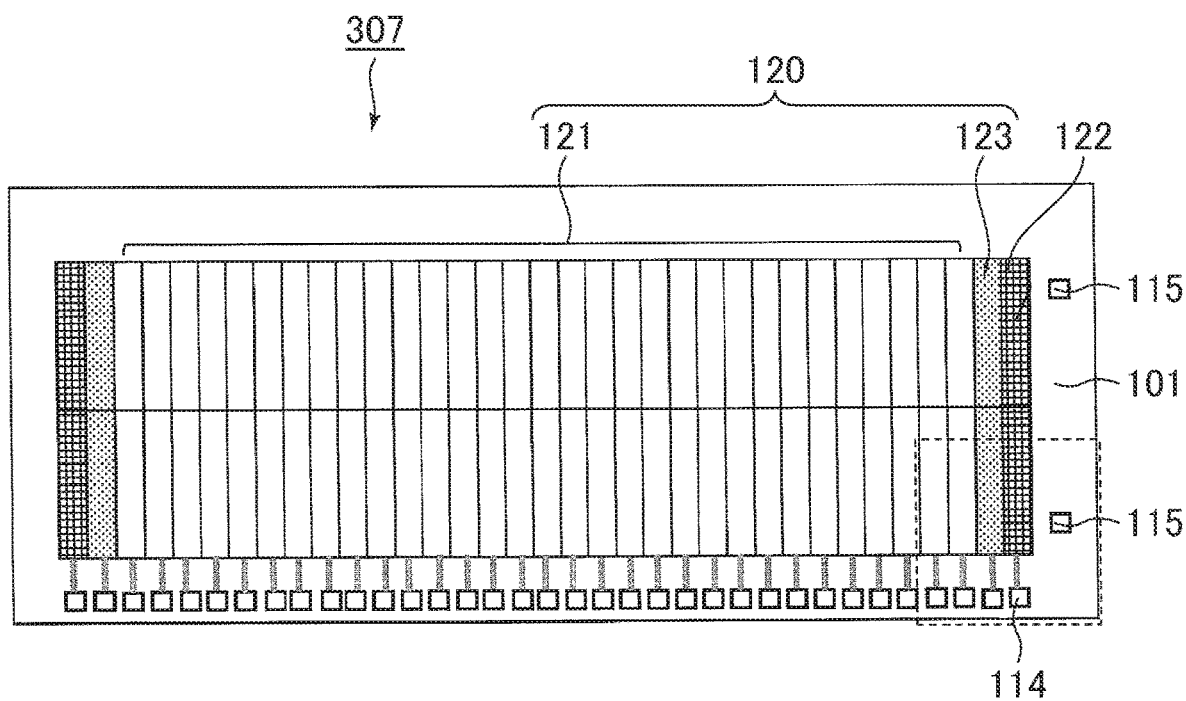
FIG. 3 is a general view showing an array for explaining an embodiment of an ultrasonic probe according to the present invention.
Figure 4:
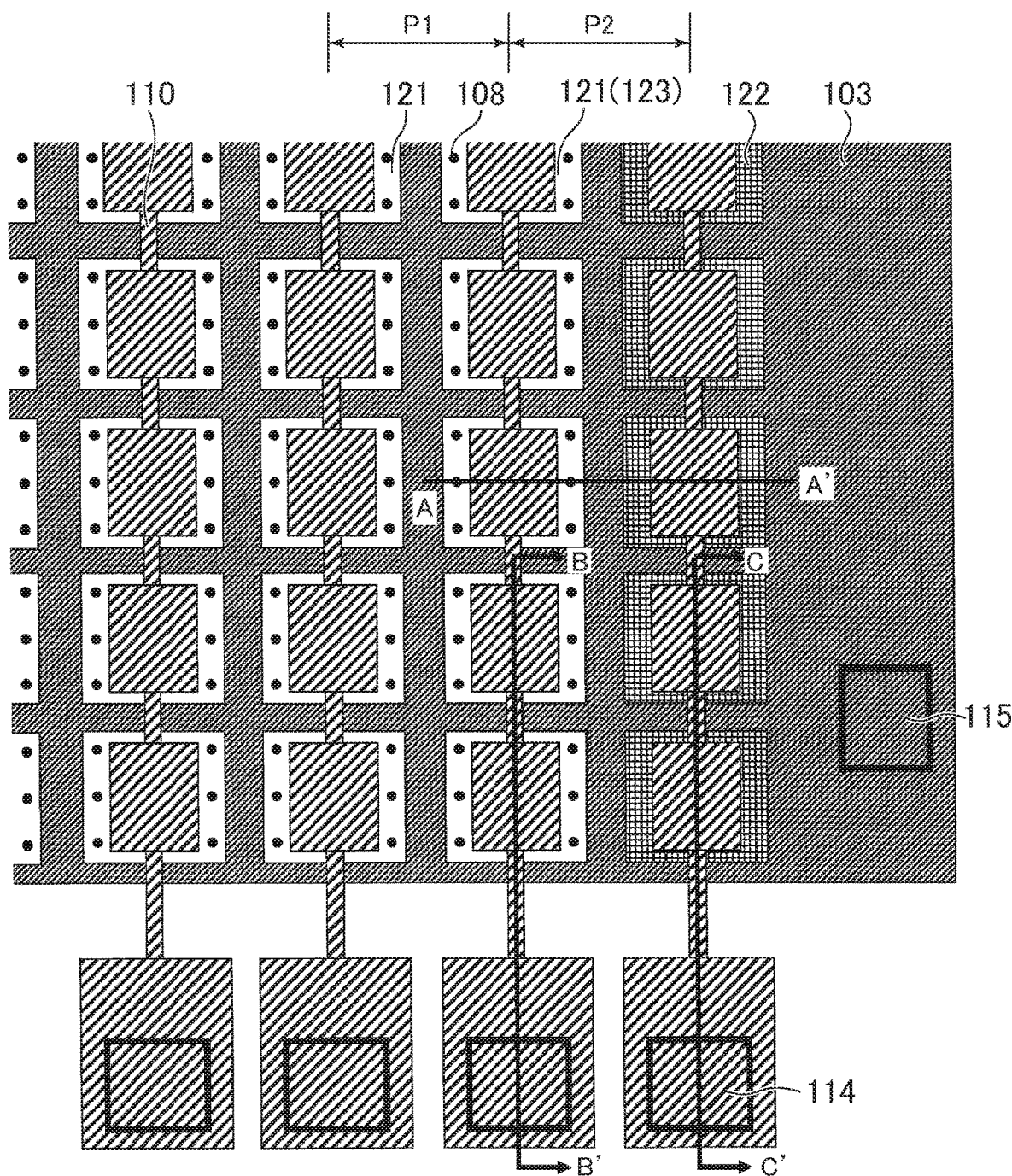
FIG. 4 is a plan view showing a part of an ultrasonic probe equivalent to a first embodiment.

FIG. 3 shows the whole array of the ultrasonic probe in this embodiment and FIG. 4 shows a part (a part encircled by a dotted line in FIG. 3) of the array. As shown in FIG. 3, the array has structure in which plural CMUT elements 120 are arranged in a row direction (in FIG. 3, a transverse direction) and in a column direction (in FIG. 3, a lengthwise direction) and individual CMUT element 120 is configured by plural ultrasonic cells 121. The CMUT elements 120 arranged in the row direction are connected to the common lower electrode (a lower electrode pad 115) for every row and the CMUT elements 120 arranged in the column direction are connected to a common upper electrode (an upper electrode pad 114) every column. The lower electrode 103 and the upper electrode 110 are respectively connected to a driving circuit not shown via the electrode pads 115, 114 as shown in FIG. 4. Each CMUT element 120 can be selectively driven by selectively driving the electrode (the lower electrode) in each row and the electrode (the upper electrode) in each column by the driving circuit. In FIG. 4, to facilitate understanding relation between the lower electrode 103 and the upper electrode 110 in the cell, a substrate 101 (see FIG. 3) and other elements are not shown.

Plural reference cells 122 having a common membrane (the lower electrode, insulating films and the like) configuring together with the ultrasonic cell 121 and having the same shape as the ultrasonic cell 121 are arranged in the same array as the ultrasonic cell 121 in the CMUT element 120 on both sides in the row direction of the array. The plural reference cells 122 are connected to the lower electrode 103 common to the ultrasonic cells 121 respectively adjacent in the row direction and the reference cells are connected to the common upper electrode 110.

The ultrasonic cell 121 adjacent to the reference cell 122 out of the ultrasonic cells 121 has the same structure as the other ultrasonic cells 121; however, it is desirable that the adjacent ultrasonic cell functions as a dummy cell 123 unused for transmitting/receiving an ultrasonic wave. As shown in FIG. 4, when the reference cell 122 is arranged next to the ultrasonic cell 121, sound pressure transmitted by the ultrasonic cell 121 adjacent to the reference cell 122 may be different from sound pressure transmitted by the ultrasonic cell 121 which is not adjacent to the reference cell 122 even if similar voltage is applied to all the ultrasonic cells 121. The reason is that rigidity of the ultrasonic cell 121 adjacent to the reference cell 122 and rigidity of the ultrasonic cell 121 which is not adjacent to the reference cell 122 are different and the difference comes from displacement of the membrane of both. The displacement of the membrane of all the ultrasonic cells 121 in the ultrasonic transducer is equalized by making the ultrasonic cell 121 adjacent to the reference cell 122 function as a dummy cell as described above and transmitted sound pressure can be made uniform. When the ultrasonic probe is driven and an ultrasonic wave is transmitted from the ultrasonic cell 121, no AC voltage is applied to the dummy cell 123 and only DC voltage is applied. Or neither AC voltage nor DC voltage is applied to the dummy cell 123.

In FIG. 4, the case that the reference cell 122 is arranged at equal pitch P1=P2 to the array of the ultrasonic cells 121 is shown; however, when the ultrasonic cell adjacent to the reference cell is made to function as a dummy cell, pitch P2 between the dummy cell 123 and the reference cell 122 is not necessarily required to be equal to pitch P1 between the ultrasonic cells. For example, P2 may be shorter than P1.

Further, in FIG. 3, the case that the reference cells 122 are arranged on both sides in the row direction of the array in consideration of a transmitting/receiving function of the ultrasonic probe is shown; however, the reference cell 122 is not necessarily required to be arranged on both sides in the row direction. Moreover, it is desirable in view of a function described later of the reference cell 122 that reference cells are arranged on both sides, although the reference cell may also be arranged only on one side.

Further, in FIG. 4, the case that the lower electrode 103 is common to all cells (called a cell by integrating the ultrasonic cell and the reference cell) is shown; however, the lower electrode 103 may also be physically divided. When the divided lower electrode 103 is made the same potential, it is an equivalent circuit to the configuration shown in FIG. 4. Furthermore, in FIG. 4, the case that a shape of the cell (a cavity and the upper electrode) viewed from a top face is a quadrangle is shown; however, the shape is not limited to the quadrangle and may also be a polygon such as a hexagon and a circle. However, it is important that the area of a part in which the lower electrode and the upper electrode are overlapped is equal in all cells when the all the cells are viewed from the top face.

Figure 5:
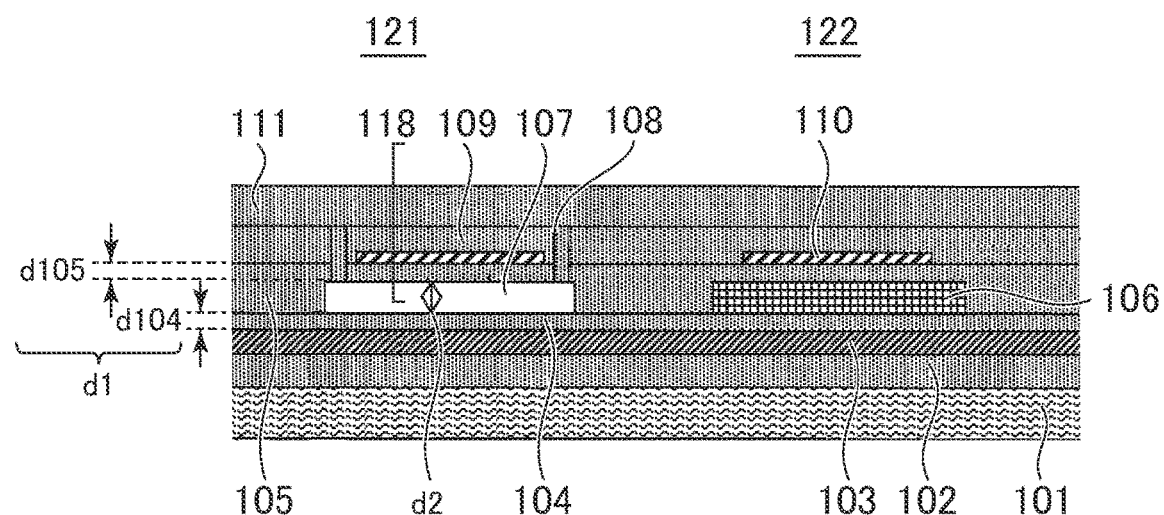
FIG. 5 is a sectional view viewed along a line A-A' in FIG. 4.
Figure 6:
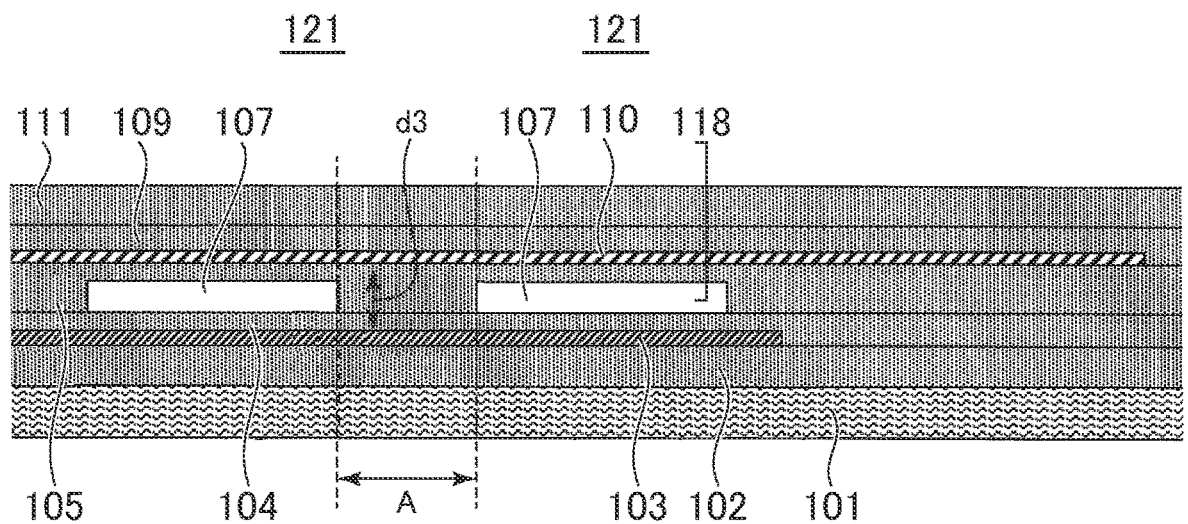
FIG. 6 is a sectional view viewed along a line B-B' in FIG. 4.
Figure 7:
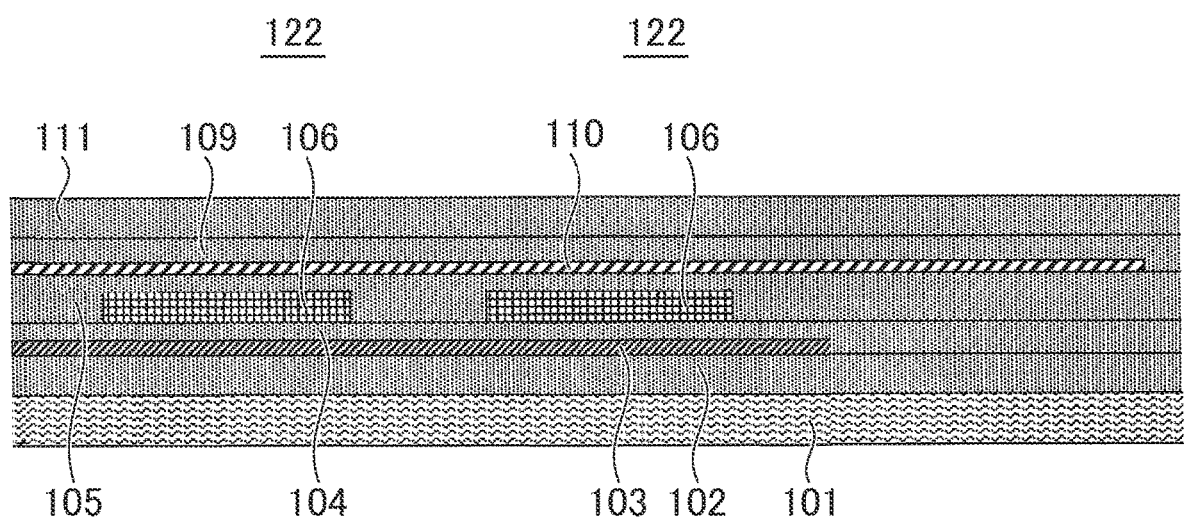
FIG. 7 is a sectional view viewed along a line C-C' in FIG. 4.

Next, the structure of the cell will be described referring to FIGS. 5 to 7. FIG. 5 is a sectional view viewed along a line A-A' in FIG. 4 and shows the ultrasonic cell and the reference cell respectively arranged in the row direction. FIG. 6 is a sectional view viewed along a line B-B' in FIG. 4 and shows plural ultrasonic cells arranged in the column direction, FIG. 7 is a sectional view viewed along a line C-C' in FIG. 4, and FIG. 7 shows plural reference cells arranged in the column direction. In these drawings, the same reference numeral is allocated to the same component and the duplicate description is omitted.

The ultrasonic cell 121 is a cell used for transmitting/receiving an ultrasonic wave, has structure in which a cavity 107 is arranged in a part between the lower electrode 103 formed on a substrate 101 via an insulating film 102 and the upper electrode 110 located over the lower electrode as shown in FIG. 6, and the cavity 107 is encircled by insulating films 104, 105 so as to insulate the lower electrode 103 and the upper electrode 110. An insulating film 111 is further formed on the upper electrode 110. A membrane 118 configured by the insulating film 105, the upper electrode 110 and the insulating film 111 and located on the cavity 107 is oscillated by applying voltage between the lower electrode 103 and the upper electrode 110 so as to generate voltage difference and temporally varying applied voltage. As for the two ultrasonic cells 121 shown in FIG. 6, the lower electrode 103 and the upper electrode 110 are common and the two ultrasonic cells simultaneously generate an ultrasonic wave.

The reference cell 122 has the same structure as the ultrasonic cell 121 except that the cavity 107 of the ultrasonic cell 121 shown in FIG. 6 is replaced with metal 106 as shown in FIG. 7 and an array (a layout) in the column direction is also the same. That is, the reference cell 122 and the ultrasonic cell 121 share the substrate 101 as shown in FIG. 5 and share the same insulating films 102, others and the same lower electrode 103. Hereby, parasitic capacity caused in the reference cell 122 and the ultrasonic cell 121 can be substantially equalized and parasitic capacity caused in the ultrasonic cell 121 can be corrected utilizing the reference cell 122 (described later).

Figure 8:
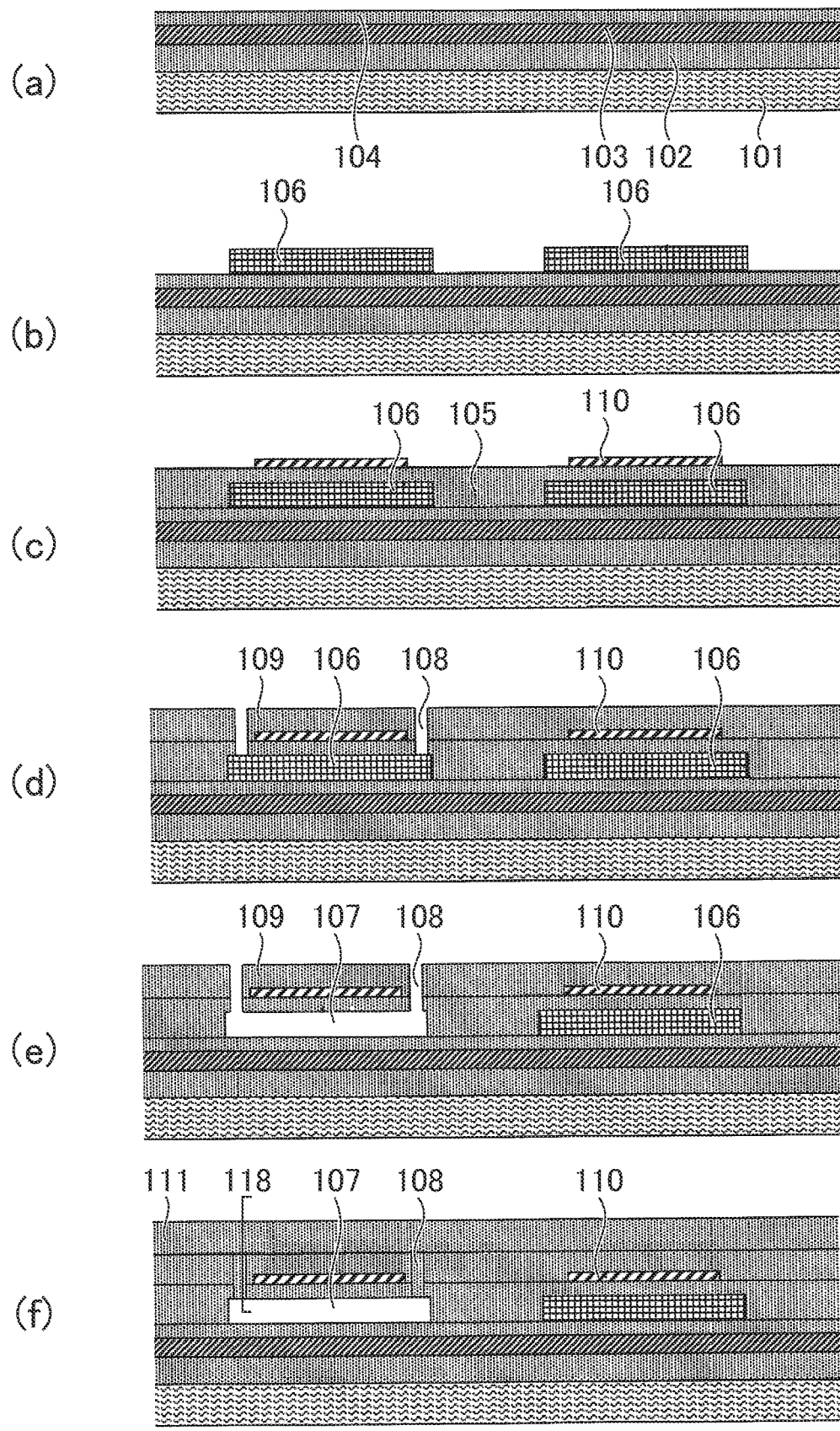
FIGS. 8(a) to (f) show one example of a method of manufacturing the ultrasonic probe shown in FIG. 1.

Next, an embodiment of a method for manufacturing CMUT having the abovementioned structure will be described. FIG. 8 shows one example of a manufacturing procedure.

First, as shown in FIG. 8(a), an insulating film 102, a lower electrode 103 and an insulating film 104 are sequentially formed on (over) a substrate 101. For the substrate 101, a semiconductor substrate made of monocrystalline silicon and the like is used. The insulating films 102, 104 can be a single-layer or laminated film made of one or two types of materials concretely selected out of silicon oxide ($SiO_2$), silicon nitride ($Si_3N_4$), aluminum oxide ($Al_2O_3$), titanium oxide ($TiO_2$), zirconium oxide ($ZrO_2$), hafnium oxide ($HfO_2$) and the like. Further, the insulating films 102, 104 may also be made of the same material or may also be made of different materials; however, as to the insulating film 102, materials having a satisfactory adhesive property to materials of the substrate and the lower electrode formed over the substrate are selected, and it is desirable that the insulating film 104 is made of a material having high withstand voltage, for example, $SiO_2$ because the insulating film is a part in which a high electric field is generated. For the lower electrode 103 formed on the insulating film 102, metal such as tungsten, aluminum, titanium, chromium and copper or a metallic conductive material is used. The lower electrode 103 can be configured by a single-layer or laminated film made of these materials.

The insulating film 102, the lower electrode (the conductive film) 103 and the insulating film 104 respectively described above can be formed by well-known film formation technology such as plasma CVD and a deposition method.

Next, a metal film 106 is formed on the insulating film 106 by sputtering and the like. For materials of the metal film 106, metal or a metallic conductive material can be used and especially, tungsten (W), titanium (Ti) and titanium nitride (TiN) are preferable in consideration of removability by etchant in a later etching process and etching selectivity. The metal film 106 is a layer provided only for forming a cavity 107 as to the ultrasonic cell and is also called a sacrificial layer. The thickness of the sacrificial layer determines cavity height 107 and the sacrificial layer is formed to have very uniform thickness. The thickness is 0.1 to 1.0 μm for example.

The metal film 106 is patterned using lithography and dry etching for example as shown in FIG. 8(b). In the example shown in FIG. 4, a pattern of the metal films 106 is a pattern in which quadrangles are arrayed at predetermined pitch in two-dimensional directions.

Next, after an insulating film 105 is deposited to cover the metal film 106 as shown in FIG. 8(c), an upper electrode 110 is formed. For materials of the insulating film 105, similar materials to those used for the abovementioned insulating film 104 and the like can be used, and materials having high withstand voltage are desirable like the insulating film 104. Similar materials to those used for the lower electrode 103 can be used for the upper electrode 110. The upper electrode 110 is also patterned using lithography and dry etching like the metal film 106 after an upper electrode layer is formed overall on a top face of the insulating film 105. A pattern of the upper electrodes 110 has the similar layout to the metal films 106 as shown in FIG. 4. In FIG. 4, the upper electrode 110 is represented to be within the area of the metal film 106 in a top view, although the upper electrode may also include the outside of the area of the metal film 106. At this time, overlapped area the upper electrode 110 and the lower electrode 103 shall be equalized in all cells.

Afterward, as shown in FIG. 8(d), after an insulating film 109 is deposited to cover the upper electrode 110, a cavity forming hole 108 is formed. The cavity forming hole 108 is a hole for injecting etchant for removing the metal film 106 as a sacrificial layer and is provided so that the cavity forming hole pierces the insulating films 105, 109 in plural locations along a periphery of the upper electrode 110 and reaches the metal film 106. It is in only a cell to be an ultrasonic cell 121 that the cavity forming hole 108 is formed and no cavity forming hole 108 is formed in a cell to be a reference cell 122. In an example shown in FIG. 8(d), the leftward cell becomes an ultrasonic cell and the rightward cell becomes a reference cell.

Etchant is injected through the cavity forming hole 108, the metal film 106 is dissolved as shown in FIG. 8(e), and a cavity 107 is formed. For the etchant, etchant for selectively dissolving the material of the metal film 106, for example, tungsten without dissolving the insulating films which encircle the cavity 107, for example, a sulfuric acid peroxide mixture acquired by mixing sulfuric acid and hydrogen peroxide solution and the like can be used. After the cavity 107 is formed by etching, the insulating film 111 is deposited to cover overall and the cavity forming hole 108 is sealed as shown in FIG. 8(f). The insulating films 109, 111 configure the membrane together with the upper electrode 110 and the membrane is displaced in transmitting/receiving an ultrasonic wave. At that time, it is desirable that the membrane before displacement is flat. Therefore, it is desirable that plural layers are laminated using a material having tensile stress such as SiN, a material having compressive stress such as $SiO_2$ and the like for the insulating films 109, 111 so as to secure flatness.

The CMUT where a cell in which the cavity 107 is formed, that is, an ultrasonic cell 121 and a cell in which no cavity 107 is formed and the metal film 106 is left without being dissolved, which is a reference cell 122, are formed over the same substrate is manufactured by the abovementioned manufacturing method.

In manufacturing the CMUT in this embodiment, it is important that each film configuring the ultrasonic cell 121 and each film configuring the reference cell 122 are common and are formed in the same steps and for materials configuring each film (layer) and film formation methods, a well-known material and method can be adopted in place of those without limiting to those shown in the example as long as those do not hinder the performance of a final product.

In the CMUT manufactured as described above, the cavity 107 theoretically has uniform height determined by the metal film 106 which is a sacrificial layer. Accordingly, the cavity height 107 that determines maximum transmission sound pressure of the CMUT is theoretically determined by thickness of the metal film 106; actually, however, the cavity height is not necessarily fixed depending upon the precision of film formation technique of each film configuring the cell, temperature and temporal variation in manufacture and use and the like, and the cavity height 107 is required to be precisely evaluated.

As for the ultrasonic probe in this embodiment, the performance of the ultrasonic cell can be precisely evaluated utilizing the reference cell 122 by using the CMUT provided with the reference cell having the same structure and the common films as/to the ultrasonic cell on/over the same substrate for the ultrasonic transducer. Especially, an effect of parasitic capacity is expelled utilizing electrostatic capacity of the reference cell and precision in calculating the cavity height can be enhanced. Examples of evaluating performance include receiving sensitivity, the estimate of a life of the ultrasonic cell and the like as well.

For one example of evaluating the performance of the ultrasonic cell 121 utilizing the reference cell 122, a method of calculating the cavity height 107 of the ultrasonic cell 121 will be described below.

When the CMUT is driven as an ultrasonic probe, it is important to estimate its maximum transmission sound pressure so as to determine optimum driving voltage or so as to estimate a life of the CMUT. Since the maximum transmission sound pressure depends upon the cavity height 107 in the ultrasonic cell 121, the maximum transmission sound pressure can be calculated if only the cavity height 107 is known and consequently, it is required to measure the precise cavity height 107. In this embodiment, the cavity height is calculated on the basis of measured electrostatic capacity of the ultrasonic cell. In this case, since parasitic capacity is also included in addition to proper electrostatic capacity in the electrostatic capacity of the measured cell, an error caused by the parasitic capacity is included in the cavity height calculated on the basis of the electrostatic capacity of the ultrasonic cell. Then, in this calculating method, electrostatic capacity of the reference cell is measured so as to reduce an error caused by parasitic capacity. The method of calculating the cavity height in the ultrasonic cell using the electrostatic capacity of the reference cell will be described below.

The calculating method will be described in comparison between the ultrasonic cell 121 and the reference cell 122 respectively adjacent in the row direction and shown in FIG. 5. In the ultrasonic cell 121, the upper electrode 110 and the lower electrode 103 are opposite via the insulating films 105, 104 and the cavity 107, and holds electrostatic capacity. In the meantime, in the reference cell 122, the upper electrode 110 and the lower electrode 103 are opposite via the insulating films 105, 104 and the metal film 106, and holds electrostatic capacity.

The electrostatic capacity C of the ultrasonic cell 121 can be expressed by an expression (1).

[Mathematical expression 1]

$$C = \varepsilon_0 \frac{S}{d_1 + d_2} + C_p \quad (1)$$

In this expression, $\varepsilon_0$ denotes a dielectric constant in vacuum, S denotes overlapped area in a top view of the upper electrode 110 and the lower electrode 103, $d_1$ denotes distance acquired by multiplying total thickness of the insulating films 105, 104 between the upper electrode 110 and the lower electrode 103 by an inverse number of a relative dielectric constant, $d_2$ denotes the cavity height 107, and $C_p$ denotes parasitic capacity caused by the upper electrode 110 and the lower electrode 103 in a region except the ultrasonic cell 121.

$\varepsilon_0$ is a constant, the area S is the same as the area of the upper electrode 110 in the CMUT in which the common lower electrode 103 is provided overall in all cells as shown in FIG. 4, and the area S is a designed value. Further, $d_1$ is expressed in an expression (2), and as the total thickness $(d_{105}+d_{104})$ of the insulating films 105, 104 between the upper electrode 110 and the lower electrode 103 is a designed value and the relative dielectric constant $\varepsilon$ of the insulating films is a constant determined depending upon materials of the insulating films, $d_1$ can be calculated in the expression (2).

[Mathematical expression 2]

$$d_1 = (d_{105}+d_{104}) \times (1/\varepsilon) \quad (2)$$

Accordingly, when the parasitic capacity $C_p$ is acquired in the expression (1), the height $d_2$ of the cavity 107 can be acquired using the measured electrostatic capacity C. $C_p$ can be theoretically calculated; actually, however, an error is caused, and it is difficult to precisely acquire the cavity height. Then, the parasitic capacity $C_p$ is calculated on the basis of the electrostatic capacity of the reference cell 122. The electrostatic capacity Cref of the reference cell 122 can be expressed in an expression (3).

[Mathematical expression 3]

$$C_{ref} = \varepsilon_0 \frac{S}{d_1} + C_{p\text{-}ref} \quad (3)$$

In this expression, Cp-ref denotes parasitic capacity caused by the upper electrode 110 and the lower electrode 103 in a region except the reference cell 122.

When $C_p$ in the expression (1) and Cp-ref in the expression (3) are equal, the electrostatic capacity C of the ultrasonic cell 121 and the electrostatic capacity Cref of the reference cell 122 are measured and the height $d_2$ of the cavity can be calculated in an expression (4) on the basis of difference in measured electrostatic capacity between both cells.

[Mathematical expression 4]

$$d_2 = \frac{\varepsilon_0 S d_1}{d_1(C - C_{ref}) + \varepsilon_0 S} - d_1 \quad (4)$$

As described above, when the parasitic capacity $C_p$ of the ultrasonic cell 121 and the parasitic capacity Cp-ref of the reference cell 122 are equal, the cavity height can be precisely evaluated in the expression (4) on the basis of results of measuring the electrostatic capacity C of the ultrasonic cell 121 and the electrostatic capacity Cref of the reference cell 122.

The parasitic capacity $C_p$ of the ultrasonic cell 121 and the parasitic capacity Cp-ref of the reference cell 122 are mainly caused by a conductor that exists in the region except cells and are respectively expressed in the following expressions (5), (6).

[Mathematical expression 5]

$$C_p = \varepsilon_0 \frac{S_p}{d_3} \quad (5)$$

[Mathematical expression 6]

$$C_{p\text{-}ref} = \varepsilon_0 \frac{S_{p\text{-}ref}}{d_{3\text{-}ref}} \quad (6)$$

In these expressions, $S_p$ denotes overlapped area of the upper electrode 110 and the lower electrode 103 in the top view in the region in which the parasitic capacity in the electrostatic capacity of the ultrasonic cell 121 is caused except the ultrasonic cell 121, and $d_3$ denotes distance acquired by multiplying the thickness of the insulating films between the upper electrode 110 and the lower electrode 103 in the overlapped area $S_p$ by the inverse number of the relative dielectric constant. Similarly, Sp-ref denotes overlapped area of the upper electrode 110 and the lower electrode 103 in the top view in the region in which the parasitic capacity in the electrostatic capacity of the reference cell 122 is caused except the reference cell 122, and d3-ref denotes distance acquired by multiplying the thickness of the insulating films between the upper electrode 110 and the lower electrode 103 in the overlapped area Sp-ref by the inverse number of the relative dielectric constant. FIG. 6 shows relation between a region A in which the upper electrode and the lower electrode are overlapped except cells and $d_3$.

To equalize the parasitic capacity Cp and Cp-ref, it is known from the expressions (5), (6) that $S_p$ and $d_3$ of the ultrasonic cell 121 and Sp-ref and d3-ref of the reference cell 122 have only to be equalized.

As the ultrasonic cell 121 and the reference cell 122 respectively shown in FIG. 4 are arranged in the same layout, the area of the region A in which the upper electrode and the lower electrode are overlapped in the region except cells can be substantially the same in contrast between the ultrasonic cell 121 and the reference cell 122 respectively in the same row, and the difference in the area between both can be reduced. To reduce difference in parasitic capacity, since it is important that the area of the regions A is the same, the difference in parasitic capacity can be reduced in configurations having the same area of the regions A even if layouts, array pitch, contours and the like are different as in the embodiment shown in FIG. 4.

Further, as shown in FIG. 6, the insulating film 105, the insulating film 104 and the cavity 107 are provided between the upper electrode 110 and the lower electrode 103 of the ultrasonic cell 121. In the meantime, the insulating film 105, the insulating film 104, and the metal film 106 are provided between the upper electrode 110 and the lower electrode 103 of the reference cell 122, and the ultrasonic cell 121 and the reference cell 122 have common structure except the cavity 107 of the ultrasonic cell 121 and the metal film 106 of the reference cell 122. Hereby, the difference in distance between the electrodes ($d_3$, d3-ref) in the regions A in which parasitic capacity of the ultrasonic cell 121 and the reference cell 122 is caused can be reduced.

Further, to reduce the difference in distance between the electrodes in the regions A in which parasitic capacity is caused, it is also effective that the ultrasonic cell 121 and the reference cell 122 are arranged as close as possible. The reason is that the difference in thickness between the insulating films 105 and the insulating film 104 between the upper electrode 110 and the lower electrode 103 of the ultrasonic cell 121 and the reference cell 122 decreases as distance between both cells is closer because of a property of deposition equipment. In the embodiment shown in FIG. 4, from a viewpoint of transmission/reception characteristics of an ultrasonic wave, since the reference cell 122 is arranged outside array structure of the ultrasonic cells 121, the cavity height of the closer ultrasonic cell to the reference cell 122 can be precisely calculated. Accordingly, from a viewpoint of precisely evaluating the cavity height in the ultrasonic cell 121, the reference cell may also be arranged anywhere in the ultrasonic transducer without limiting to the arrangement of the reference cell shown in FIG. 4, and arrangement that the reference cells are distributed in plural positions in the row direction may also be adopted. It need scarcely be said that even if the reference cell is arranged apart from the ultrasonic cell 121, fixed effect can be acquired.

The cavity height in the ultrasonic cell can be calculated at various times such as before and after individual CMUT is divided from the substrate (a wafer) in manufacturing CMUT, before and after the CMUT is built in the ultrasonic probe. Further, even after the ultrasonic probe is used, the cavity height can be calculated as a part of subsequent quality management. Since the height of a cavity sometimes varies due to thermal strain and mechanical strain in a mounting process even if a CMUT chip having desired cavity height is acquired at the stage of the wafer, it is important so as to maintain the performance of the ultrasonic probe that the cavity height can be precisely evaluated after the chip is mounted in the ultrasonic probe. It can be checked whether desired maximum transmission sound pressure can be acquired or not by precisely evaluating cavity height and a life of the CMUT can be estimated.

Figure 9:
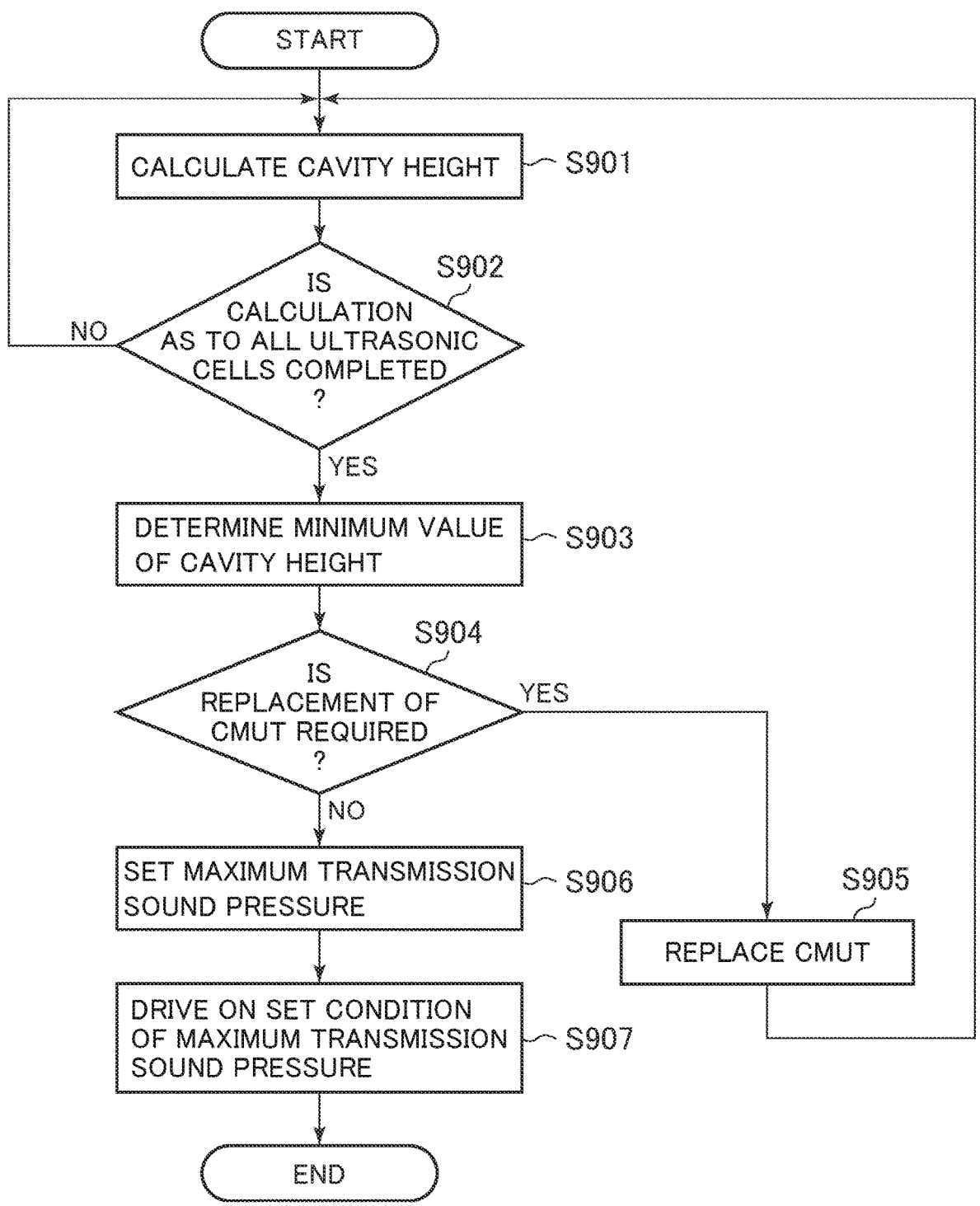
FIG. 9 is a flowchart showing one example of a method of measuring height of a cavity in an ultrasonic cell.

FIG. 9 shows a procedure for evaluating cavity height after building in the ultrasonic probe. The cavity height in the individual ultrasonic cell configuring the CMUT is sequentially calculated in the abovementioned expression (4) using electrostatic capacity Cp-ref measured as to the reference cell in a position (for example, in the closest position in the same row) corresponding to the ultrasonic cell (S901). This calculation is performed as to all ultrasonic cells (S902), and the minimum value is searched out of the calculated cavity height of all the ultrasonic cells (S903). In the cell having the lowest cavity in height, the insulating films between the electrodes in the cell have the highest field intensity, dielectric breakdown is readily caused, and the cell has the shortest life. Then, when the searched minimum value is equal to or below a preset threshold, the replacement of the CMUT is instructed (S904, S905). When the minimum value of the cavity height is larger than the threshold, a condition on which desired maximum transmission sound pressure is acquired is set with the minimum value as a criterion (S906) and the ultrasonic probe is driven (S907).

Another requirement led from cavity height such as the dispersion of cavity height calculated as to each ultrasonic cell is evaluated or an additional requirement may also be used for replacing the CMUT with new one. Hereby, the uniformity of sound pressure every ultrasonic cell can be secured.

FIG. 9 shows the procedure in the case that the ultrasonic probe is driven immediately next to the measurement of cavity height; however, the measurement of cavity height can also be performed as a procedure separate from the drive of the ultrasonic probe, that is, ultrasonography. Further, the measurement of cavity height may also be performed in the ultrasonic diagnostic apparatus shown in FIG. 2 and provided with a function (a performance evaluation device 317) for evaluating the performance of the ultrasonic probe and can also be performed by dedicated measurement equipment. In the former case, the performance evaluation device 317 of the ultrasonic diagnostic apparatus measures electrostatic capacity of each ultrasonic cell and each reference cell in the ultrasonic transducer configuring the ultrasonic probe when an instruction to evaluate the performance of the ultrasonic probe is input via GUI (the operator console 304) displayed on a display 303 for example, and stores each measured value in a memory. Next, according to a flow shown in FIG. 9, the cavity height of each ultrasonic cell is calculated and finally, results of the evaluation are displayed on the display 303. For the display of evaluation results, display that maximum transmission sound pressure desired by an operator is achieved and there is no problem, display that replacement should be made, display that timing of replacement approaches and the like are possible. Further, the height of the individual cavity, its minimum value and the like can also be displayed.

As for the ultrasonic probe (for example, see FIG. 4) adopting the CMUT provided with each ultrasonic cell and each reference cell respectively having the lower electrode in common, the structure and the method of evaluating the ultrasonic cell using it have been described above; however, the structure of the CMUT is not limited to this and variations are allowed. An embodiment in which structure is changed will be described below. In the following embodiment, the same reference numeral is allocated to the same component as that in the first embodiment and its duplicate description is omitted.

Second Embodiment

An ultrasonic probe in this embodiment has a characteristic that an upper electrode and a lower electrode of each ultrasonic cell and each reference cell are provided with independent array structure (a two-dimensional array). Though this embodiment is different in array structure from the first embodiment, an ultrasonic probe in this embodiment is similar to the ultrasonic probe in the first embodiment in that a reference cell is arranged in an ultrasonic transducer. The similar effect that height of a cavity can be precisely evaluated can be acquired by using results of measuring electrostatic capacity of the ultrasonic cell and electrostatic capacity of the reference cell.

Figure 10:
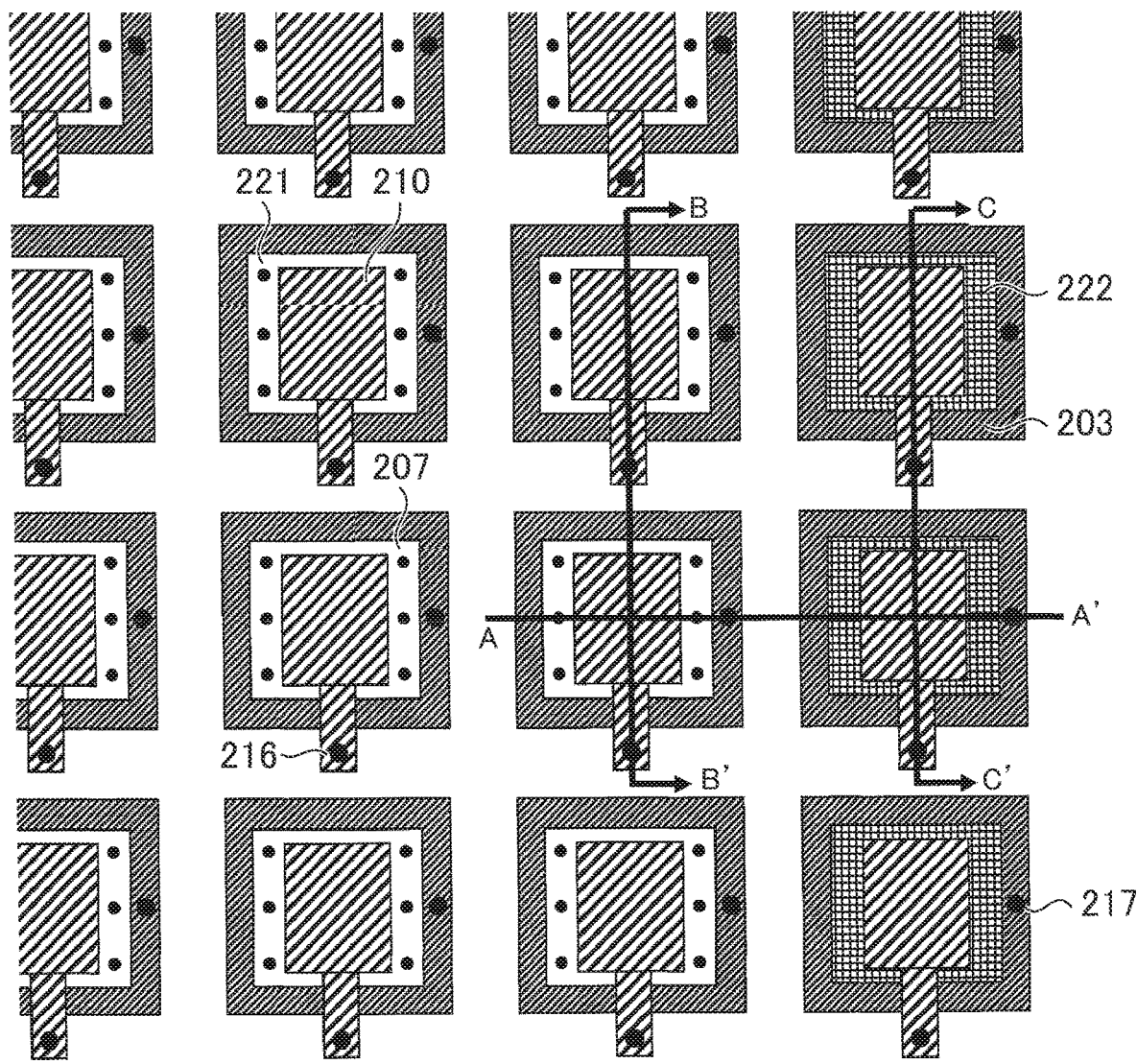
FIG. 10 is a plan view showing a part of an ultrasonic probe equivalent to a second embodiment.
Figure 11:
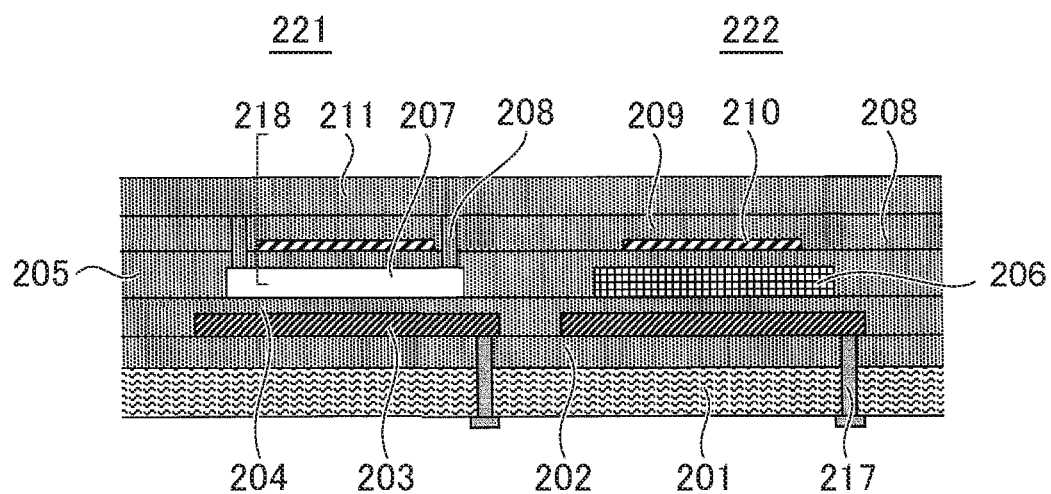
FIG. 11 is a sectional view viewed along a line A-A' in FIG. 10.
Figure 12:
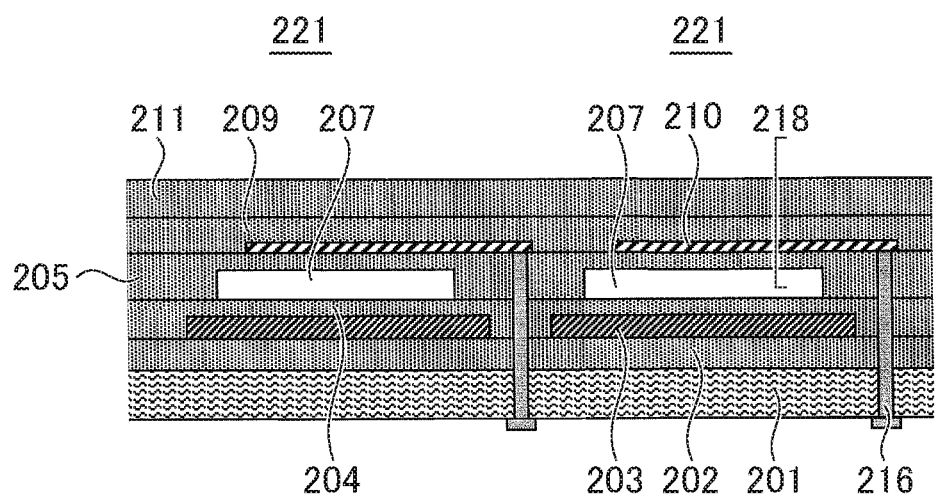
FIG. 12 is a sectional view viewed along a line B-B' in FIG. 10.
Figure 13:
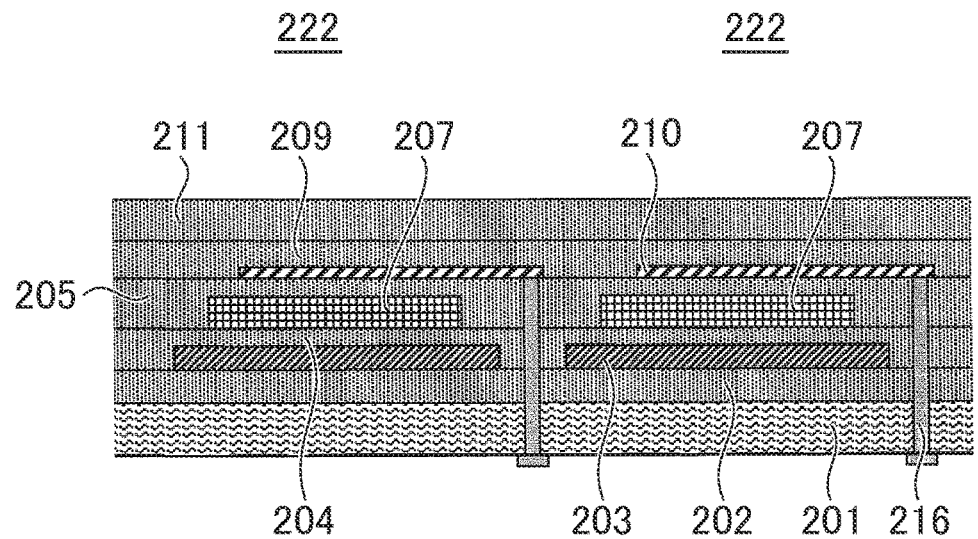
FIG. 13 is a sectional view viewed along a line C-C' in FIG. 10.

Referring to FIGS. 10 to 13, one example of the ultrasonic probe in this embodiment will be described below. FIG. 10 is a top view showing a part of the ultrasonic transducer included in the ultrasonic probe in this embodiment, FIGS. 11 to 13 are respectively a sectional view viewed along a line A-A' in FIG. 10, a sectional view viewed along a line B-B', and a sectional view viewed along a line C-C'. The whole array of the ultrasonic probe is similar to the general view shown in FIG. 2 and is omitted.

As shown in FIG. 10, in this embodiment, an ultrasonic probe array also has structure that ultrasonic cells 221 are arrayed in a row direction and in a column direction and a reference cell 222 is arranged outside the array in the row direction of the ultrasonic cells. In the drawing, a cell in which the cavity 207 is arranged in a region where an upper electrode 210 and a lower electrode 203 are overlapped in a top view is the ultrasonic cell 221 and a cell in which a metal film 206 is arranged is the reference cell 222. The ultrasonic cell 221 is a cell used for transmitting/receiving an ultrasonic wave, and the reference cell 222 is a cell for measuring parasitic capacity so as to precisely evaluate cavity height in the ultrasonic cell 221. The ultrasonic cell adjacent to the reference cell 222 may also be a dummy cell unused for transmitting/receiving an ultrasonic wave in driving.

The ultrasonic cell 221 and the reference cell 222 have the same structure except that the cells are different in the cavity 207 and the metal film 206, and a substrate 201, insulating films 202, 204, 205, 209, 211 are common in each cell. Further, a layout of the reference cells 222 is the same as a layout of the ultrasonic cells 221 and the reference cells are formed at the same pitch.

In the ultrasonic probe in this embodiment, both the upper electrode 210 and the lower electrode 203 in each cell are independent and to feed to these electrodes, a through electrode for the upper electrode 216 and a through electrode for the lower electrode 217 are arranged. This will be described referring to FIGS. 11 to 13 below.

In contrast of a section shown in FIG. 11 with the section shown in FIG. 5 (in the first embodiment), the respective lower electrodes 203 of the ultrasonic cell 221 and the reference cell 222 are independent and pulled up to a bottom of the substrate 201 by the through electrode for the lower electrode 217. In the two-dimensional array, the number of electrodes in the ultrasonic transducer is enormous so as to connect the upper electrodes 210/the lower electrodes 203 of the ultrasonic cells 221 and the reference cells 222 and circuits outside the ultrasonic transducer. Therefore, it is difficult in the design of the layout that the upper electrode 210 and the lower electrode 203 are formed only on the upside of the substrate 201. In the example shown in FIG. 11, the lower electrode 203 is pulled on the downside of the substrate 201 by the through electrode for the lower electrode 217 and this problem is settled.

Further, as shown in FIGS. 12, 13, each upper electrode 210 of the ultrasonic cell 121 and the reference cell 122 is pulled up to the bottom of the substrate 201 by the through electrode 216 for the upper electrode.

The ultrasonic probe in this embodiment can be manufactured by the substantially similar method to the ultrasonic probe in the first embodiment except that the lower electrode 203 is patterned after deposition, and the through electrode for the upper electrode 216 and the through electrode for the lower electrode 217 are formed. Since the ultrasonic cell and the reference cell respectively manufactured as described above have the same structure (overlapped area of the upper electrode and the lower electrode is equal) and formed by a common film, their parasitic capacity can be substantially equalized, and the evaluation of the performance of the ultrasonic cell, especially the measurement of the cavity height, can be precisely made utilizing the reference cell.

Since a method of calculating the cavity height in the ultrasonic cell using electrostatic capacity (a measured value) of the reference cell is similar to the method in the first embodiment, the description is omitted.

Figure 14:
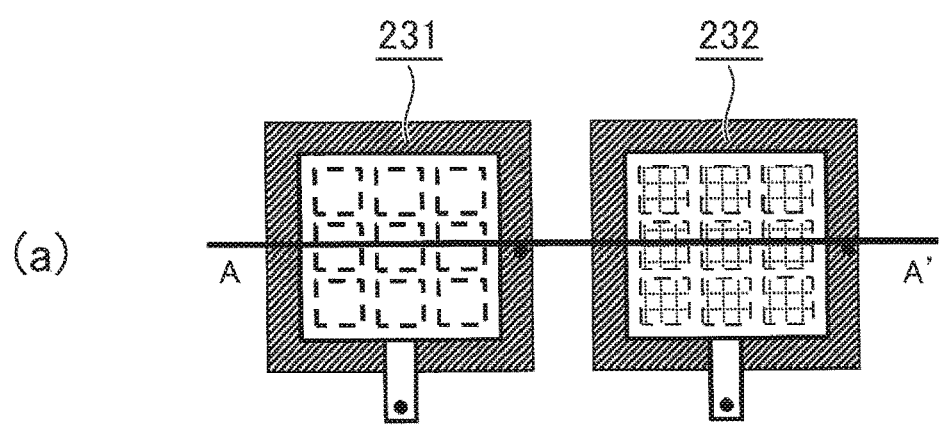
FIG. 14 show a variation of the ultrasonic probe equivalent to the second embodiment.
Figure 14:
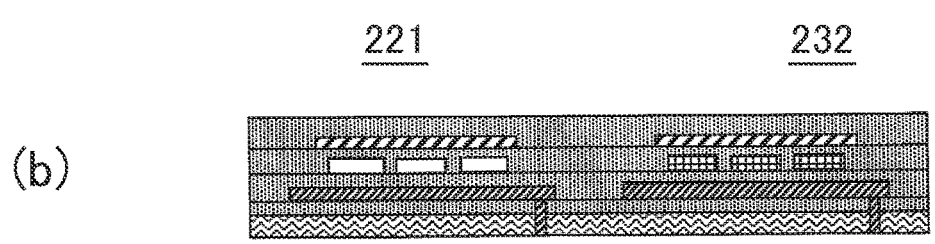

As the embodiment different in the structure of the ultrasonic probe, the configuration in which individual cell includes the independent upper electrode and the independent lower electrode is shown; however, the present invention can also be similarly applied to another array structure. For example, as shown in FIG. 14, as to array structure that one common upper electrode and one common lower electrode are provided to plural ultrasonic cells, the ultrasonic cell can also be evaluated by arranging an element 231 including plural ultrasonic cells and an element 232 having the same structure and including plural reference cells and measuring electrostatic capacity of the reference cells as in the abovementioned embodiment.

Third Embodiment

This embodiment has a characteristic that height of a cavity in an ultrasonic cell is estimated utilizing a reference cell arranged separately from an ultrasonic transducer over the same substrate as the ultrasonic transducer. That is, each of the abovementioned embodiments has the characteristic that the ultrasonic probe in which the reference cells are arranged in the ultrasonic transducer is used. In this embodiment, however, no reference cell is arranged in the ultrasonic transducer finally built in an ultrasonic probe. Instead, this embodiment has a characteristic that a reference cell is fabricated over a substrate in a manufacturing process of CMUT and the performance of the ultrasonic cell configuring plural CMUT elements (120 in FIG. 3) formed over the same substrate is evaluated utilizing the reference cell.

Figure 15:
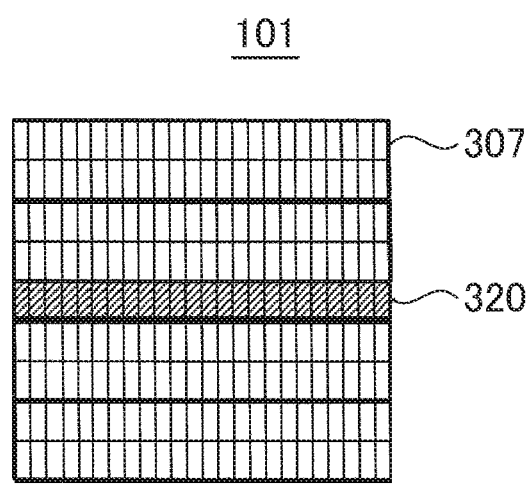
FIG. 15 illustrates one example of a method of measuring height of a cavity in an ultrasonic cell in a third embodiment.

FIG. 15 shows a state in which plural ultrasonic transducers 307 are manufactured over a substrate 101. In FIG. 15, only four ultrasonic transducers are shown for simplification. The structure of the individual ultrasonic transducer 307 has the similar structure to that of the transducer shown in FIG. 3 for example; however, all cells are an ultrasonic cell, and a reference cell acquired by replacing a cavity in the ultrasonic cell with metal is not included. Instead, an array (a reference cell array) 320 configured by plural reference cells is formed over the substrate 101 separately from the ultrasonic transducer 307. Though the following is not limited, the reference cell array 320 is provided with the same structure in the same array as an ultrasonic cell array configuring the ultrasonic transducer. However, in the ultrasonic cell, a cavity is formed between an upper electrode and a lower electrode, while in the reference cell, a part corresponding to the cavity is replaced with a metal film.

The ultrasonic cells arranged in a row direction share the lower electrode and the ultrasonic cells arranged in a column direction share the upper electrode. The cells in the reference cell array share the lower electrode and are provided with each independent upper electrode.

In such configuration, after the plural ultrasonic transducers and the reference cell array are manufactured over the substrate by the manufacturing method shown in FIG. 8 for example, cavity height in the ultrasonic cell configuring each ultrasonic transducer is evaluated as product inspection before each ultrasonic transducer is divided. An evaluation method is similar to the method described in the first embodiment and first, each electrostatic capacity of the ultrasonic cell as an object and the reference cell in a position corresponding to the ultrasonic cell is measured. The cavity height in the ultrasonic cell is calculated in the expression (4) using the electrostatic capacity of the ultrasonic cell and the electrostatic capacity of the reference cell. A product is judged non-defective or defective depending upon whether the calculated cavity height meets a predetermined threshold or not. As for this product inspection, all ultrasonic cells configuring one ultrasonic transducer may be an object of the inspection and a part of ultrasonic cells may be selected.

According to this embodiment, the reference cell having the same structure as the ultrasonic cell in the transducer and sharing a film can be utilized without fabricating a reference cell in one ultrasonic transducer and product inspection before the ultrasonic transducer is mounted in an ultrasonic probe can be performed.

INDUSTRIAL APPLICABILITY

The present invention can be applied to various types of ultrasonic probes using CMUT and the precision in transmission/reception of the ultrasonic probe can be enhanced.

LIST OF REFERENCE SIGNS

100 - - - Ultrasonic transducer (CMUT), 101, 210 - - - Substrate, 103, 203 - - - Lower electrode, 106, 206 - - - Metal film, 107, 207 - - - Cavity, 110, 210 - - - Upper electrode, 120 - - - CMUT element, 121, 221 - - - Ultrasonic cell, 122, 222 - - - Reference cell, 123 - - - Dummy cell, 300 - - - Ultrasonic diagnostic apparatus, 302 - - - Ultrasonic probe, 303 - - - Display, 304 - - - Operator console, 305 - - Main body, 306 - - - Connector to probe, 307 - - - Ultrasonic transducer, 311 - - - Ultrasonic transmitter-receiver, 312 - - - Signal processing circuit, 313 - - - Controller, 314 - - - Memory, 315 - - - Power source, 316 - - - Auxiliary device, 317 - - - Performance evaluation device.

The invention claimed is:

1. An ultrasonic probe, comprising:
a transducer having a plurality of cells arranged in an array structure, each of the plurality of cells including a lower electrode and an upper electrode arranged via a gap with respect to the lower electrode,
wherein the plurality of cells of the transducer include a plurality of ultrasonic cells, the gaps of which are void, and which transmit/receive an ultrasonic wave, a reference cell, the gap of which is filled with a conductive material, and an ultrasonic cell adjacent to the reference cell being a dummy cell which is not driven when the ultrasonic probe is driven,
wherein the array structure in which the plurality of cells are arranged is two-dimensional, and
the reference cell is arranged at an end of the array structure.

2. The ultrasonic probe according to claim 1, wherein the conductive material of the reference cell is metal.

3. The ultrasonic probe according to claim 1,
wherein each of the plurality of ultrasonic cells and the reference cell are equal in overlapped areas of the upper electrode and the lower electrode, respectively, when viewed from above the upper electrode.

4. The ultrasonic probe according to claim 1,
wherein each of the plurality of ultrasonic cells and the reference cell have same planar layouts of the upper electrode and the lower electrode.

5. The ultrasonic probe according to claim 1,
wherein the plurality of ultrasonic cells and the reference cell share the lower electrode.

6. An ultrasonic probe, comprising:
a transducer having a plurality of cells arranged in an array structure, each of the plurality of cells including a lower electrode and an upper electrode arranged via a gap with respect to the lower electrode,
wherein the plurality of cells of the transducer include a plurality of ultrasonic cells, the gaps of which are void, and which transmit/receive an ultrasonic wave, and a reference cell, the gap of which is filled with a conductive material, and
wherein the upper electrode and the lower electrode of each of the plurality of cells are independent of the upper electrode and the lower electrode of another cell of the plurality of cells.

7. An ultrasonic diagnostic apparatus, comprising:
an ultrasonic probe;
an ultrasonic transmitter-receiver that supplies a driving voltage to the ultrasonic probe;
an image generator that generates an ultrasonic image using an ultrasonic signal received by the ultrasonic transmitter-receiver; and
a controller that controls the ultrasonic transmitter-receiver,
wherein the ultrasonic probe includes a transducer having a plurality of cells arranged in an array, each of the plurality of cells including a lower electrode and an upper electrode arranged via a gap with respect to the lower electrode, and
wherein the plurality of cells include an ultrasonic cell, the gap of which is void, and which transmits/receives an ultrasonic wave and a reference cell, the gap of which is filled with a conductive material, the ultrasonic diagnostic apparatus further comprising:
a performance evaluation device that determines a cavity height of the ultrasonic cell,
wherein the performance evaluation device corrects a measured electrostatic capacity of the ultrasonic cell using a measured electrostatic capacity of the reference cell and calculates the cavity height of the ultrasonic cell.

* * * * *